(12) United States Patent
Gray et al.

(10) Patent No.: US 6,274,372 B1
(45) Date of Patent: Aug. 14, 2001

(54) RHODOCOCCUS FLAVIN REDUCTASE COMPLEMENTING DSZA AND DSZC ACTIVITY

(75) Inventors: Kevin A. Gray; John D. Childs; Charles H. Squires, all of The Woodlands, TX (US)

(73) Assignee: Enchira Biotechnology Corporation, The Woodlands, TX (US)

(*) Notice: Subject to any disclaimer, the term of this patent is extended or adjusted under 35 U.S.C. 154(b) by 0 days.

(21) Appl. No.: 09/304,214

(22) Filed: May 3, 1999

Related U.S. Application Data (62) Division of application No. 09/105,057, filed on Jun. 26, 1998, now Pat. No. 5,919,683, which is a division of application No. 08/735,963, filed on Oct. 23, 1996, now Pat. No. 5,804,433.

(51) Int. Cl.[7] .............................. C10G 32/00; C12N 9/20
(52) U.S. Cl. ................... 435/282; 435/189; 435/252.3; 435/252.33; 435/281; 536/23.2
(58) Field of Search ................... 435/189, 252.3, 435/252.33, 281, 282; 536/23.2

(56) References Cited

U.S. PATENT DOCUMENTS

| | | | |
|---|---|---|---|
| 4,562,156 | 12/1985 | Isbister et al. | 435/253 |
| 5,002,888 | 3/1991 | Kilbane, II | 435/252.31 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,870 | 10/1994 | Monticello et al. | 435/282 |
| 5,484,723 | 1/1996 | Zenno et al. | 435/189 |

FOREIGN PATENT DOCUMENTS

| | | |
|---|---|---|
| 96/17940 | 6/1996 | (WO). |

OTHER PUBLICATIONS

Piddington, C. S., et al., "Sequence and Molecular Characterization of DNA Region Encoding the Dibenzothiophene Desulfurization Operon of Rhodococcus sp. Strain IGTS8," *App. Env. Microbiol.*, 61(2): 468–475 (1995).

Blanc, V., et al., Cloning and Analysis of Structural Genes from *Streptomyces pristinaespiralis* Encoding Enzymes Involved in the Conversion of Pristinamycin IIB to Pristinamycin IIA (PIIA): PIIA Synthase and NADH: Riboflavin 5'–Phosphate Oxidoreductase,*J. of Bacteriology*, 177(18): 5206–5214 (Sep. 1995).

Thibaut, D., et al., Purification of the Two–Enzyme System Catalyzing the Oxidation of the D–Proline Residue of Pristinamycin IIB during the Last Step of Pristinamycin IIA Biosynthesis, *J. of Bacteriology*, 177(18): 5199–5205 (Sep. 1995).

Denome, S.A., et al., "Characterization of Desulfurization Genes from Rhodococcus sp. Strain IGTS8," *J. Bact.*, 176(21): 6707–6716 (1994).

Ohshiro, T., et al., "Enzymatic Desulfurization of Dibenzothiophene by a Cell–Free System of *Rhodococcus erythropolis* D–1," *FEMS Microbiology Letters*, 118: 341–344 (1994).

Ohshiro, T., et al., "Involvement of Flavin Coenzyme in Dibenzothiophene Degrading Enzyme System from *Rhodococcus erythropolis* D–1," *Biosci. Biotech. Biochem.*, 59(7): 1349–1351 (1995).

Nagy, I., et al., "Characterization of the Rhodococcus sp. NI86/21 gene encoding alcohol: N,N'–dimethyl–4–nitrosoaniline oxidoreductase inducible by atrazine and thiocarbamate herbicides,"*Arch. Microbiol.*, 163: 439–446 (1995).

Parry, R.J., et al., "Cloning, Analysis, and Overexpression of the Gene Encoding Isobutylamine N–Hydroxylase from the Valanimycin Producer, *Streptomyces viridifaciens,"J. of Bacteriology* 179(2): 409–416 (1997).

Arunachalam, U., et al., "p–Hydroxyphenylacetate–e–hydroxylase," *The J. of Biological Chem.*, 267(36): 25848–25855 (1992).

Lei, B. and Tu, S.C., "Gene Overexpression, Purification, and Identification of a Desulfurization Enzyme from Rhodococcus sp. Strain EGTS8 as a Sulfide/Sulfoxide Monooxygenase," *J. of Bacteriology*, 178(19): 5699–5705 (1996).

Kendrew, S.G., et al., "Identification of a Flavin:NADH Oxidoreductase Involved in the Biosynthesis of Actinorhodin," *The J. of Biological Chem.*, 270(29): 17339–17343 (1995).

Knobel, H.–R., et al., "Cloning and Characterization of the Genes Encoding Nitrilotriacetate Monooxygenase of *Chelatobacter heintzii* ATCC 29600," *J. of Bacteriology*, 178(21): 6123–6132 (1996).

Fernandez–Moreno, M., et al., "Nucleotide Sequence and Deduced Functions of a Set of Cotranscribed Genes of *Streptomyces coelicolor* A3(2) Including the Polyketide Synthase for the Antibiotic Actinorhodin*," *The J. of Biological Chem.*, 267(27): 19278–19290 (1992).

(List continued on next page.)

*Primary Examiner*—Nashaat T. Nashed
(74) *Attorney, Agent, or Firm*—Hamilton, Brook, Smith & Reynolds, P.C.

(57) ABSTRACT

The invention provides a novel flavin reductase, which has been isolated from Rhodococcus strain sp. IGTS8 and purified to homogeneity. The flavin reductase is of use in the biocatalytic desulfurization of a fossil fuel containing organic sulfur compounds. The method comprises the steps of (1) contacting the fossil fuel with an aqueous phase containing a biocatalyst capable of cleaving carbon—sulfur bonds and a rate-enhancing amount of the flavin reductase of the present invention, thereby forming a fossil fuel and aqueous phase mixture; (2) maintaining the mixture under conditions sufficient for cleavage of the carbon—sulfur bonds of the organic sulfur molecules by the biocatalyst, thereby resulting in a fossil fuel having a reduced organic sulfur content; and (3) separating the fossil fuel having a reduced organic sulfur content from the resulting aqueous phase.

12 Claims, 2 Drawing Sheets

OTHER PUBLICATIONS

Arunachalam, U., et al., "Mechanism of p–Hydroxyphenylacetate–e–hydroxylase," *The J. of Biological Chem.*, 269(1): 150–155 (1994).

Prieto, M.A. and Garcia, J.L., "Molecular Characterization of 4–Hydroxyphenylacetate 3–Hydroxylase of *Escherichia coli,*" *The J. of Biological Chem.*, 269(36): 22823–22829 (1994).

Gray, K.A., et al., "Molecular mechanisms of Biocatalytic desulfurization of fossil fuels," *Nature Biotechnology*, 14: 1705–1709 (1996).

Xi, L., et al., "A Flavin Reductase Stimulates DszA and DszC Proteins of *Rhodococcus erythropolis* EGTS8 in Vitro," *Biochemical and Biophysical Research Communications*, 230: 73–75 (1997).

Li, M.Z., et al., "Cloning and Overexpression of an NADH–FMN Oxidoreductase gene (frdA) of *Rhodococcus erythropolis* IGTS8 involved in the oxidative desulfurization of fossil fuels," Abstracts of the General Meeting of the American Society for Microbiology, vol. 97, No. O–106, p. 436 (May 4, 1997).

ACTCCGAACT CCTCCGAATC ACCGCCGGCC TCGCCGTCGA CATGGACTGA AGCACTTCAG

CCAGCCCGGT CCGAAACCAC TCAGACGTGC GTCCACCTAT AGTTGGACGC ACCATGTGCA

CTGCAACCAG GACCCCGGCC GGCAACCACT GGCGTCGACG GCACGTAGAT CTGTGCCGCA

CCGACGCATG TCTGTGTATG CCGAGCGCAG TCACCTCGAC CACACCGCAC ACCTCGAGTT

```
                                                          BsmI
                                                           |
CCAGCCGGAG AGTTCCCG TTG TCT GAC AAG CCG AAT GCC GTT TCC AGC CAC
                    Met Ser Asp Lys Pro Asn Ala Val Ser Ser His
                            forward primer
```

```
ACC ACC CCC GAC GTC CCC GAA GTA GCG GCG ACG CCC GAG TTG TCC ACC
Thr Thr Pro Asp Val Pro Glu Val Ala Ala Thr Pro Glu Leu Ser Thr
        probe
```

```
GGC ATC TGC GCC GGT GAC TAC CGC GCT GCG CTT CGC CGC CAC CCC GCC
Gly Ile Cys Ala Gly Asp Tyr Arg Ala Ala Leu Arg Arg His Pro Ala
```

```
GGT GTC ACC GTC GTG ACC CTC GAT TCG GGT ACC GGC CCG GTG GGT TTC
Gly Val Thr Val Val Thr Leu Asp Ser Gly Thr Gly Pro Val Gly Phe
```

```
ACC GCC ACC TCG TTC TCG TCC GTC TCC CTC GAG CCG CCG CTC GTC TCG
Thr Ala Thr Ser Phe Ser Ser Val Ser Leu Glu Pro Pro Leu Val Ser
```

```
TTC AAC ATC GCG GAG ACG TCG TCG AGC ATC AAT GCA CTC AAG GCA GCC
Phe Asn Ile Ala Glu Thr Ser Ser Ser Ile Asn Ala Leu Lys Ala Ala
```

```
GAG TCC TTG GTG ATC CAC CTT CTC GGC GAA CAT CAG CAG CAT CTG GCC
Glu Ser Leu Val Ile His Leu Leu Gly Glu His Gln Gln His Leu Ala
```

```
CAG CGC TTT GCG CGT AGT GCC GAT CAG CGT TTT GCA GAC GAG TCA CTG
Gln Arg Phe Ala Arg Ser Ala Asp Gln Arg Phe Ala Asp Glu Ser Leu
```

```
TGG GCA GTG CTC GAC ACC GGG GAA CCG GTG CTG CAC GGC ACC CCC AGC
Trp Ala Val Leu Asp Thr Gly Glu Pro Val Leu His Gly Thr Pro Ser
```

```
TGG ATG CGC GTC AAG GTC GAC CAG CTG ATC CCT GTC GGC GAC CAC ACG
Trp Met Arg Val Lys Val Asp Gln Leu Ile Pro Val Gly Asp His Thr
```

```
CTG GTC ATC GGA CTC GTC ACG CGG GTT CAC GCC GAA GAA GAC GAC GAA
Leu Val Ile Gly Leu Val Thr Arg Val His Ala Glu Glu Asp Asp Glu
                                      reverse primer
```

```
TCC GCT GCC GCG CCG CTG CTC TAC CAC GAG GGC AAG TAC TAC CGC CCG
Ser Ala Ala Ala Pro Leu Leu Tyr His Glu Gly Lys Tyr Tyr Arg Pro
```

```
ACT CCG TTA GGT CAA TAGACAACTG TGCGCCTTTA TTAACCGCCC GCGGTTAATA
Thr Pro Leu Gly Gln
```

AAGGCGCACA GCAAGTTAGA GCGCTACGTA CTTGGTATCG AGATACTCGT CGATACCCTC

GGTTCCGCCT TCACGGCCGA A

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 955 base pairs
      (B) TYPE: nucleic acid
      (C) STRANDEDNESS: single
      (D) TOPOLOGY: linear    (ii) MOLECULE TYPE: DNA (genomic)

(ix) FEATURE:
      (A) NAME/KEY: CDS
      (B) LOCATION: 259..834

(xi) SEQUENCE DESCRIPTION: SEQ ID NO:1:

ACTCCGAACT CCTCCGAATC ACCGCCGGCC TCGCCGTCGA CATGGACTGA AGCACTTCAG    60

-continued

```
CCAGCCCGGT CCGAAACCAC TCAGACGTGC GTCCACCTAT AGTTGGACGC ACCATGTGCA      120

CTGCAACCAG GACCCCGGCC GGCAACCACT GGCGTCGACG GCACGTAGAT CTGTGCCGCA      180

CCGACGCATG TCTGTGTATG CCGAGCGCAG TCACCTCGAC CACACCGCAC ACCTCGAGTT      240

CCAGCCGGAG AGTTCCCG TTG TCT GAC AAG CCG AAT GCC GTT TCC AGC CAC       291
                    Leu Ser Asp Lys Pro Asn Ala Val Ser Ser His
                     1           5                      10

ACC ACC CCC GAC GTC CCC GAA GTA GCG GCG ACG CCC GAG TTG TCC ACC       339
Thr Thr Pro Asp Val Pro Glu Val Ala Ala Thr Pro Glu Leu Ser Thr
             15                  20                  25

GGC ATC TGC GCC GGT GAC TAC CGC GCT GCG CTT CGC CGC CAC CCC GCC       387
Gly Ile Cys Ala Gly Asp Tyr Arg Ala Ala Leu Arg Arg His Pro Ala
         30                  35                  40

GGT GTC ACC GTC GTG ACC CTC GAT TCG GGT ACC GGC CCG GTG GGT TTC       435
Gly Val Thr Val Val Thr Leu Asp Ser Gly Thr Gly Pro Val Gly Phe
     45                  50                  55

ACC GCC ACC TCG TTC TCG TCC GTC TCC CTC GAG CCG CCG CTC GTC TCG       483
Thr Ala Thr Ser Phe Ser Ser Val Ser Leu Glu Pro Pro Leu Val Ser
 60              65                  70                      75

TTC AAC ATC GCG GAG ACG TCG TCG AGC ATC AAT GCA CTC AAG GCA GCC       531
Phe Asn Ile Ala Glu Thr Ser Ser Ser Ile Asn Ala Leu Lys Ala Ala
                 80                  85                  90

GAG TCC TTG GTG ATC CAC CTT CTC GGC GAA CAT CAG CAG CAT CTG GCC       579
Glu Ser Leu Val Ile His Leu Leu Gly Glu His Gln Gln His Leu Ala
             95                  100                 105

CAG CGC TTT GCG CGT AGT GCC GAT CAG CGT TTT GCA GAC GAG TCA CTG       627
Gln Arg Phe Ala Arg Ser Ala Asp Gln Arg Phe Ala Asp Glu Ser Leu
         110                 115                 120

TGG GCA GTG CTC GAC ACC GGG GAA CCG GTG CTG CAC GGC ACC CCC AGC       675
Trp Ala Val Leu Asp Thr Gly Glu Pro Val Leu His Gly Thr Pro Ser
125                 130                 135

TGG ATG CGC GTC AAG GTC GAC CAG CTG ATC CCT GTC GGC GAC CAC ACG       723
Trp Met Arg Val Lys Val Asp Gln Leu Ile Pro Val Gly Asp His Thr
140                 145                 150                 155

CTG GTC ATC GGA CTC GTC ACG CGG GTT CAC GCC GAA GAA GAC GAC GAA       771
Leu Val Ile Gly Leu Val Thr Arg Val His Ala Glu Glu Asp Asp Glu
                160                 165                 170

TCC GCT GCC GCG CCG CTG CTC TAC CAC GAG GGC AAG TAC TAC CGC CCG       819
Ser Ala Ala Ala Pro Leu Leu Tyr His Glu Gly Lys Tyr Tyr Arg Pro
             175                 180                 185

ACT CCG TTA GGT CAA TAGACAACTG TGCGCCTTTA TTAACCGCCC GCGGTTAATA       874
Thr Pro Leu Gly Gln
             190

AAGGCGCACA GCAAGTTAGA GCGCTACGTA CTTGGTATCG AGATACTCGT CGATACCCTC      934

GGTTCCGCCT TCACGGCCGA A                                                955
```

(2) INFORMATION FOR SEQ ID NO:2:

(i) SEQUENCE CHARACTERISTICS:
        (A) LENGTH: 192 amino acids
        (B) TYPE: amino acid
        (D) TOPOLOGY: linear     (ii) MOLECULE TYPE: protein     (xi) SEQUENCE DESCRIPTION: SEQ ID NO:2:

```
Leu Ser Asp Lys Pro Asn Ala Val Ser Ser His Thr Thr Pro Asp Val
 1               5                  10                  15

Pro Glu Val Ala Ala Thr Pro Glu Leu Ser Thr Gly Ile Cys Ala Gly
             20                  25                  30
```

```
Asp Tyr Arg Ala Ala Leu Arg Arg His Pro Ala Gly Val Thr Val Val
        35                  40                  45

Thr Leu Asp Ser Gly Thr Gly Pro Val Gly Phe Thr Ala Thr Ser Phe
    50                  55                  60

Ser Ser Val Ser Leu Glu Pro Pro Leu Val Ser Phe Asn Ile Ala Glu
65                  70                  75                  80

Thr Ser Ser Ser Ile Asn Ala Leu Lys Ala Ala Glu Ser Leu Val Ile
                85                  90                  95

His Leu Leu Gly Glu His Gln Gln His Leu Ala Gln Arg Phe Ala Arg
            100                 105                 110

Ser Ala Asp Gln Arg Phe Ala Asp Glu Ser Leu Trp Ala Val Leu Asp
            115                 120                 125

Thr Gly Glu Pro Val Leu His Gly Thr Pro Ser Trp Met Arg Val Lys
    130                 135                 140

Val Asp Gln Leu Ile Pro Val Gly Asp His Thr Leu Val Ile Gly Leu
145                 150                 155                 160

Val Thr Arg Val His Ala Glu Glu Asp Asp Glu Ser Ala Ala Ala Pro
                165                 170                 175

Leu Leu Tyr His Glu Gly Lys Tyr Tyr Arg Pro Thr Pro Leu Gly Gln
            180                 185                 190

(2) INFORMATION FOR SEQ ID NO:3:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ser Asp Lys Pro Asn Ala Val Ser Ser His Thr Thr Pro Asp Val Pro
1               5                   10                  15

Glu Val Ala Ala Thr Pro Glu Leu Ser Thr Gly Ile Ala Ala Gly Asp
                20                  25                  30

Tyr Arg Ala Ala Leu Arg Ser His
        35                  40

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Val His Ala Glu Glu Asp Asp Glu Ser Ala Ala Ala Pro Leu Leu Tyr
1               5                   10                  15

Tyr Glu Gly (2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:5:

Tyr Tyr Xaa Pro Thr Pro Leu
1               5

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Tyr Tyr Arg Pro Thr Pro Leu Gly Gln Lys
1               5                   10

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GAYAARCCNA AYGCNGT                                                      17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAYACNACNC CNGAYGT                                                      17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TCRTCRTCYT CYTCNGCRTG                                                   20

RHODOCOCCUS FLAVIN REDUCTASE COMPLEMENTING DSZA AND DSZC ACTIVITY

RELATED APPLICATION

This application is a Divisional Application of Ser. No. 09/105,057, filed on Jun. 26, 1998, now U.S. Pat. No. 5,919,683 which is a Divisional Application of Ser. No. 08/735,963, filed on Oct. 23, 1996, now U.S. Pat. No. 5,804,433. The teachings of each of these referenced applications are expressly incorporated herein by reference in their entirety.

BACKGROUND OF THE INVENTION

The microbial desulfurization of fossil fuels has been an area of active investigation for over fifty years. The object of these investigations has been to develop biotechnology based methods for the pre-combustion removal of sulfur from fossil fuels, such as coal, crude oil and petroleum distillates. The driving forces for the development of desulfurization methods are the increasing levels of sulfur in fossil fuel and the increasingly stringent regulation of sulfur emissions. Monticello et al., "Practical Considerations in Biodesulfurization of Petroleum," IGT's 3d Intl. Symp. on Gas, Oil, Coal and Env. Biotech., (Dec. 3–5, 1990) New Orleans, La.

Many biocatalysts and processes have been developed to desulfurize fossil fuels, including those described in U.S. Pat. Nos. 5,356,801, 5,358,870, 5,358,813, 5,198,341, 5,132,219, 5,344,778, 5,104,801 and 5,002,888, incorporated herein by reference. Economic analyses indicate that one limitation in the commercialization of the technology is improving the reaction rates and specific activities of the biocatalysts, such as the bacteria and enzymes that are involved in the desulfurization reactions. The reaction rates and specific activities (sulfur removed/hour/gram of biocatalyst) that have been reported in the literature are much lower than those necessary for optimal commercial technology. Therefore, improvements in the longevity and specific activity of the biocatalyst are desirable.

SUMMARY OF THE INVENTION

The invention relates to the isolation and characterization of a novel NADH:FMN oxidoreductase (FMN\FMNH$_2$=oxidize\reduced flavin mononucleotide; NAD$^+$\NADH=oxidize\reduced nicotinamide adenine dinucleotide) from the bacterium Rhodococcus strain sp. IGTS8 (ATCC 53968), and the observation that this enzyme activates two monooxygenases, DszA and DszC, involved in the desulfurization of fossil fuels. Neither DszA nor DszC is active when purified, but enzymatic activity is restored upon addition of this novel enzyme. It is believed that this enzyme serves to couple the oxidation of NADH to substrate oxygenation by catalyzing the reaction:

FMN+NADH→FMNH$_2$+NAD$^+$.

Subsequently, FMNH$_2$ interacts with O$_2$ to form an activated oxygen species which is then transferred to dibenzothiophene (DBT) by DszC and to dibenzothiophene-5,5-dioxide (DBTO$_2$) by DszA.

The invention is thus drawn to the isolated NADH:FMN oxidoreductase (also referred to herein as 'flavin reductase') and isolated homologues and fragments thereof. The novel flavin reductase of the present invention has been purified to homogeneity and has an apparent monomeric molecular weight of 25 kDa. The enzyme contains no tightly bound flavin cofactor, but appears to utilize flavin mononucleotide (FMN) as a dissociable substrate. The enzyme activates the monooxygenase enzymes DszA and DszC in a process displaying saturation kinetics.

In another embodiment, the enzyme includes an isolated nucleotide sequence, such as a DNA or RNA sequence or molecule, encoding the novel flavin reductase, or a homologue or fragment thereof. The invention also includes a recombinant microorganism containing one or more recombinant nucleic acid molecules which encode the novel flavin reductase. The microorganism can further comprise one or more recombinant nucleic acid molecules which encode a biocatalyst capable of catalyzing one or more steps in a process for desulfurizing a fossil fuel containing organic sulfur molecules.

In a further embodiment, the invention provides a method of using the novel flavin reductase in the biocatalytic desulfurization of a fossil fuel containing organic sulfur compounds. The method comprises the steps of (1) contacting the fossil fuel with an aqueous phase containing a biocatalyst capable of cleaving carbon—sulfur bonds (such as DszA, DszB and/or DszC) and a rate-enhancing amount of the flavin reductase of the present invention, thereby forming a fossil fuel and aqueous phase mixture; (2) maintaining the mixture under conditions sufficient for cleavage of the carbon—sulfur bonds of the organic sulfur molecules by the biocatalyst, thereby resulting in a fossil fuel having a reduced organic sulfur content; and (3) separating the fossil fuel having a reduced organic sulfur content from the resulting aqueous phase.

The invention also relates to a method of enhancing the rate of biodesulfurization of a carbonaceous material containing organosulfur compounds. The method comprises the step of adding the flavin reductase to a biodesul-furization system in a rate-enhancing amount. This can be accomplished by adding the flavin reductase to the biocatalyst or by causing the expression or overexpression of the flavin reductase in a microorganism which serves as a biodesulfurization catalyst.

The invention also relates to a composition for use in biodesulfurization of a carbonaceous material containing organosulfur molecules, such as a fossil fuel. The composition comprises (a) a biocatalyst capable of desulfurizing a fossil fuel containing organic sulfur molecules and (b) the flavin reductase.

BRIEF DESCRIPTION OF THE DRAWINGS

FIG. 1 sets forth the DNA sequence (SEQ ID NO: 1) and the corresponding amino acid sequence (SEQ ID NO: 2) of the flavin reductase gene.

DETAILED DESCRIPTION OF THE INVENTION

The present invention is based on the isolation and characterization of a novel enzyme having NADH:flavin oxidoreductase activity from Rhodococcus strain sp. IGTS8 (ATCC No. 53968). The gene encoding this enzyme, designated frr, has also been isolated and cloned. An enzyme having NADH:flavin oxidoreductase activity catalyzes the reaction:

$$FMN+NADH+H^+ \rightarrow FMNH_2+NAD^+.$$

The enzyme is of use, for example, in enhancing the rate of biocatalytic fossil fuel desulfurization, possibly by transferring reducing equivalents, via $FMNH_2$, from NADH to the biocatalyst.

The present invention additionally relates to a method of desulfurizing a carbonaceous material containing organic sulfur compounds, such as a fossil fuel. The method comprises the steps of (1) contacting the carbonaceous material with an aqueous phase containing a biocatalyst capable of cleaving carbon—sulfur bonds and a rate-enhancing amount of the flavin reductase of the present invention, thereby forming a carbonaceous material and aqueous phase mixture; (2) maintaining the mixture of step (1) under conditions sufficient for cleavage of the carbon—sulfur bonds of the organic sulfur molecules by the biocatalyst, thereby resulting in a carbonaceous material having a reduced organic sulfur content; and (3) separating the carbonaceous material having a reduced organic sulfur content from the resulting aqueous phase.

The invention also includes a method for enhancing the rate of a biocatalytic reaction of a carbonaceous material containing organosulfur compounds, such as a fossil fuel. The method comprises the steps of (1) contacting the carbonaceous material with an aqueous phase containing a biocatalyst capable of oxidizing carbon—sulfur bonds and a rate-enhancing amount of an NADH:FMN oxidoreductase; (2) maintaining the mixture of step (1) under conditions sufficient for the reaction of the organosulfur compounds catalyzed by the biocatalyst.

In both methods discussed above, the flavin reductase can be added to the reaction mixture in a rate-enhancing amount. A "rate-enhancing amount", as defined herein, is an amount which will significantly increase the rate of desulfurization of the biocatalyst, as originally obtained. For example, where the biocatalyst is IGTS8, a cell-free fraction or purified enzyme preparation thereof, a "rate-enhancing amount" of the flavin reductase is an amount of the flavin reductase that, in addition to that native to the biocatalyst as obtained, will significantly increase the rate of desulfurization. The rate of desulfurization can be restored or increased, for example, by at least 25%, 50%, 100% or more in comparison to the rate employing the biocatalyst per se. The enhancement of biodesulfurization rates has also been discussed in co-pending U.S. patent applications Ser. Nos. 08/351,754 and 08/583,118, each of which is incorporated herein by reference.

In the petroleum extraction and refining arts, the term "organic sulfur" is generally understood as referring to organic molecules having a hydrocarbon framework to which one or more sulfur atoms are covalently joined. These sulfur atoms can be directly bonded to the hydrocarbon framework, e.g., by one or more carbon—sulfur bonds, or can be present in a substituent bonded to the hydrocarbon framework of the molecule, e.g., a sulfate group (which contains a carbon-oxygen-sulfur covalent linkage). The general class of organic molecules having one or more sulfur heteroatoms are sometimes referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked to adjacent carbon atoms in the hydrocarbon framework by aromatic carbon—sulfur bonds are referred to as "sulfur-bearing heterocycles". Examples of sulfur-bearing heterocycles are thiophene, benzothiophene, and dibenzothiophene.

Sulfur-bearing heterocycles are known to be stable to conventional desulfurization treatments, such as hydrodesulfurization (HDS). Sulfur-bearing heterocycles can have relatively simple or relatively complex chemical structures. In complex heterocycles, multiple condensed aromatic rings, one or more of which can be heterocyclic, are present. The difficulty of desulfurization increases with the structural complexity of the molecule. That is, refractory behavior is most accentuated in complex sulfur-bearing heterocycles, such as dibenzothiophene (DBT, $C_{12}H_8S$).

DBT is a sulfur-bearing heterocycle that has a condensed, multiple aromatic ring structure in which a five-membered thiophenic ring is flanked by two six-membered benzo rings. Much of the residual post-HDS organic sulfur in fossil fuel refining intermediates and combustible products is thiophenic sulfur. The majority of this residual thiophenic sulfur is present in DBT and derivatives thereof having one or more alkyl or aryl groups attached to one or more carbon atoms present in one or both flanking benzo rings. DBT itself is accepted in the relevant arts as a model compound illustrative of the behavior of the class of compounds encompassing DBT and derivatives thereof in reactions involving thiophenic sulfur (Monticello and Finnerty, *Ann. Rev. Microbiol.*, 39: 371–389 (1985)). DBT and derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom (Monticello and Finnerty (1985), supra). Another characteristic of DBT and derivatives thereof is that, following a release of fossil fuel into the environment, these sulfur-bearing heterocycles persist for long periods of time without significant biodegradation. Gundlach et al., *Science* 221 : 122–129 (1983). Thus, most prevalent naturally occurring microorganisms do not effectively metabolize and break down sulfur-bearing heterocycles.

A fossil fuel that is suitable for desulfurization treatment according to the present invention is one that contains organic sulfur. Such a fossil fuel is referred to as a "substrate fossil fuel". Substrate fossil fuels that are rich in thiophenic sulfur are particularly suitable for desulfurization according to the method described herein. Examples of such substrate fossil fuels include Cerro Negro or Orinoco heavy crude oils; Athabascan tar and other types of bitumen; petroleum refining fractions such as light cycle oil, heavy atmospheric gas oil, and No. 1 diesel oil; and coal-derived liquids manufactured from sources such as Pocahontas #3, Lewis-Stock, Australian Glencoe or Wyodak coal.

Biocatalytic desulfurization (biocatalysis or BDS) is the excision (liberation or removal) of sulfur from organosulfur compounds, including refractory organosulfur compounds such as sulfur-bearing heterocycles, as a result of the selective, oxidative cleavage of carbon—sulfur bonds in said compounds by a biocatalyst. BDS treatment yields the desulfurized combustible hydrocarbon framework of the former refractory organosulfur compound, along with inorganic sulfur substances which can be readily separated from each other by known techniques such as fractional distillation or water extraction. For example, DBT is converted into hydroxybiphenyl when subjected to BDS treatment. BDS is carried out by a biocatalyst comprising one or more non-human organisms (e.g., microorganisms) that functionally express one or more enzymes that direct, singly or in concert with each other, the removal of sulfur from organosulfur compounds, including sulfur-bearing heterocycles, by the selective cleavage of carbon—sulfur bonds in said compounds; one or more enzymes obtained from such microorganisms; or a mixture of such microorganisms and enzymes. Organisms that exhibit biocatalytic activity are referred to herein as being $Dsz^+$. Organisms that lack biocatalytic activity are referred to herein as being $Dsz^-$.

The biocatalysts of use herein are, generally, known in the art. Several investigators have reported the genetic modification of naturally-occurring bacteria into mutant strains capable of catabolizing DBT. Kilbane, J. J., *Resour. Cons. Recycl.* 3: 69–79 (1990), Isbister, J. D., and R. C. Doyle, U.S. Pat. No. 4,562,156 (1985), and Hartdegan, F. J. et al., *Chem. Eng. Progress:* 63–67 (1984). For the most part, these mutants desulfurize DBT nonspecifically, and release sulfur in the form of small organic sulfur breakdown products. Thus, a portion of the fuel value of DBT is lost through this microbial action. Isbister and Doyle reported the derivation of a mutant strain of Pseudomonas which appeared to be capable of selectively liberating sulfur from DBT, but did not elucidate the mechanism responsible for this reactivity.

Kilbane has reported a mixed bacterial culture which appeared capable of selectively liberating sulfur from DBT by the oxidative pathway. This culture was composed of bacteria obtained from natural sources such as sewage sludge, petroleum refinery wastewater, garden soil, coal tar-contaminated soil, etc., and maintained in culture under conditions of continuous sulfur deprivation in the presence of DBT. The culture was then exposed to the chemical mutagen 1-methyl-3-nitro- 1-nitrosoguanidine. The major catabolic product of DBT metabolism by this mutant culture was 2-hydroxybiphenyl; sulfur was released as inorganic water-soluble sulfate, and the hydrocarbon portion of the molecule remained essentially intact as 2-hydroxybiphenyl. Kilbane, J. J., *Resour. Cons. Recycl.,* 3: 69–79 (1990), the teachings of which are incorporated herein by reference.

Kilbane isolated a mutant strain of Rhodococcus from this mixed bacterial culture. This mutant, IGTS8 or ATCC No. 53968, is a particularly preferred biocatalyst for use with the instant invention. The isolation and characteristics of this mutant are described in detail in J. J. Kilbane, U.S. Pat. No. 5,104,801, the teachings of which are incorporated herein by reference. This microorganism has been deposited at the American Type Culture Collection (ATCC), 10801 University Boulevard, Manassas, Va., U.S.A. 20110-2209 under the terms of the Budapest Treaty, and has been designated as ATCC Deposit No. 53968. One suitable ATCC No. 53968 biocatalyst preparation is a culture of the living microorganisms, prepared generally as described in U.S. Pat. No. 5,104,801 and mutants or derivatives thereof. Cell-free enzyme preparations obtained from ATCC No. 53968 or mutants thereof generally as described in U.S. Pat. Nos. 5,132,219, and 5,358,870 can also be used. In the instant method for biocatalytic desulfurization (BDS), the ATCC No. 53968 biocatalytic agent can be employed in a continuous desulfurization process for the treatment of a petroleum liquid in which HDS-refractory organic sulfur molecules, such as the aromatic sulfur-bearing heterocycles, constitute a significant portion of the total organic sulfur content.

There are at least two possible types of pathways which result in the specific release of sulfur from DBT: oxidative and reductive. Preferably, an oxidative (aerobic) pathway can be followed. Examples of microorganisms that act by this oxidative pathway, preparations of which are suitable for use as the biocatalyst in the present invention include the microbial consortium (a mixture of several microorganisms) disclosed in Kilbane, *Resour. Conserv. Recycl.,* 3: 69–79 (1990), the microorganisms disclosed by Kilbane in U.S. Pat. No. 5,002,888 (issued Mar. 26, 1991), U.S. Pat. No. 5,104,801 (issued Apr. 14, 1992), U.S. Pat. Nos. 5,344,778, 5,132,219, 5,198,341, 5,356,813, 5,356,801, 5,358,870 [also described in Kilbane (1990), *Biodesulfurization: Future Prospects in Coal Cleaning,* in *Proc, 7th Ann. Int'l. Pittsburgh Coal Conf:* 373–382], and U.S. Pat. No. 5,198,341 (issued Mar. 30, 1993); and by Omori et al., *Appl. Env. Microbiol.,* 58 : 911–915 (1992); and Izumi et al., *Appl. Env. Microbiol.,* 60 :223–226 (1994) all incorporated herein by reference.

Each of the foregoing microorganisms can function as a biocatalyst in the present invention because each produces one or more enzymes (protein biocatalysts) that carry out the specific chemical reaction(s) by which sulfur is excised from refractory organosulfur compounds. Mutational or genetically engineered derivatives of any of the foregoing microorganisms, as exemplified by the U.S. patents listed above, can also be used as the biocatalyst herein, provided that appropriate biocatalytic function is retained.

Additional microorganisms suitable for use as the biocatalyst or biocatalyst source in the desulfurization process now described can be derived from naturally occurring microorganisms by known techniques. As set forth above, these methods involve culturing preparations of microorganisms obtained from natural sources such as sewage sludge, petroleum refinery wastewater, garden soil, or coal tar-contaminated soil under selective culture conditions in which the microorganisms are grown in the presence of refractory organosulfur compounds such as sulfur-bearing heterocycles as the sole sulfur source; exposing the microbial preparation to chemical or physical mutagens; or a combination of these methods. Such techniques are recounted by Isbister and Doyle in U.S. Pat. No. 4,562,156 (issued Dec. 31, 1985); by Kilbane in *Resour. Conserv. Recycl.,* 3: 69–79 (1990), U.S. Pat. Nos. 5,002,888, 5,104, 801 and 5,198,341; and by Omori and coworkers in *Appl. Env. Microbiol.,* 58: 911–915 (1992), all incorporated herein by reference.

As explained above, enzymes are protein biocatalysts made by living cells. Enzymes promote, direct or facilitate the occurrence of a specific chemical reaction or series of reactions (referred to as a pathway) without themselves becoming consumed as a result thereof. Enzymes can include one or more unmodified or post-translationally or synthetically modified polypeptide chains or fragments or portions thereof, additional coenzymes, cofactors, or coreactants which collectively catalyze the desired reaction or series of reactions. The reaction or series of reactions relevant to the present invention culminates in the excision of sulfur from the hydrocarbon framework of a refractory organosulfur compound, such as a sulfur-bearing heterocycle. The hydrocarbon framework of the former refractory organosulfur compound remains substantially intact. Microorganisms or enzymes employed as biocatalysts in the present invention advantageously do not consume the hydrocarbon framework of the former refractory organosulfur compound as a carbon source for growth. As a result, the fuel value of substrate fossil fuels exposed to BDS treatment does not deteriorate.

Although living microorganisms (e.g., a culture) can be used as the biocatalyst herein, this is not required. Biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells. Kilbane and Monticello disclose enzyme preparations that are suitable for use herein in U.S. Pat. No. 5,132,219 (issued Jul. 21, 1992), and U.S. Pat. No. 5,358,870 (filed Jun. 11, 1992), for example. Rambosek et al. disclose recombinant microorganisms and enzyme preparations, including enzymes, engineered from Rhodococcus sp. ATCC No. 53968 and suitable for use herein, in U.S. Pat. No. 5,356,801, incorporated herein by reference. In a particularly preferred embodiment, the biocatalyst is overexpressed in the recombinant host cell (such as a cell which contains more than one copy of the gene or genes). For example, the desulfurization of dibenzothiophene by Rhodococcus sp. IGTS8 has been shown to involve at least three enzymes (designated DszA, DszB and DszC), of which DszA and DszC are monooxygenases. As such, in a particularly preferred embodiment, the biocatalyst includes one or more of the enzymes DszA, DszB and/or DszC.

Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the treated fossil fuel which has been depleted of refractory organosulfur compounds.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms (e.g., ATCC No. 53968) is used as the biocatalyst preparation, a suitable culture medium lacking a sulfur source other than sulfur-bearing heterocycles can be inoculated with suitable microorganisms and fermented until a desired culture density is reached. The resulting culture can be diluted with additional medium or another suitable buffer, or microbial cells present in the culture can be retrieved e.g., by centrifugation, and resuspended at a greater concentration than that of the original culture. The concentrations of microorganism and enzyme biocatalyst can be adjusted similarly. In this manner, appropriate volumes of biocatalyst preparations having predetermined specific activities and/or concentrations can be obtained.

As discussed above, the present invention includes a novel NADH:flavin oxidoreductase, referred to hereinafter as "flavin reductase". The flavin reductase of the present invention has been isolated from Rhodococcus strain sp. IGTS8 (ATCC 53968) containing the plasmid pENOK3 (Piddington et al., *App. Env. Microbiol.*, 61 : 468–475 (1995)) as described in the Exemplification. The isolation procedure resulted in a 2400-fold purification of the enzyme to a specific activity of about 12,000 nmol NADH oxidized $min^{-1}$ (mg protein)$^{-1}$. The molecular weight as determined by denaturing sodium dodecyl sulfate-polyacrylamide gel electrophoresis (SDS-PAGE) is approximately 25 kDa. The enzyme is specific for FMN and NADH and does not accept NADPH and FAD as substrates. The flavin reductase lacks the characteristic flavin electronic absorption spectrum, and is, therefore, not a flavoprotein in that it does not include a tightly associated FMN cofactor. The enzyme instead appears to utilize FMN as a dissociable substrate.

The novel flavin reductase displays no significant sequence homology with any protein in the databases. The three characterized proteins having the greatest sequence homology with the novel flavin reductase include NADH:flavin oxidoreductases from *Streptomyces pristinaespiralis* (27% sequence homology; Thibaut et al., *J. Bact.*, 177: 5199–5205 (1995)), and "Chelatobacter" (22% sequence homology; Uetz et al., *J. Bact.*, 174: 1179–1188 (1992)).

The flavin reductase of the invention activates two monooxygenases integral to the biodesulfurization pathway, DszA and DszC. The enzyme is believed to function by coupling the oxidation of NADH with substrate oxygenation. Although a certain amount of the flavin reductase is produced by Rhodococcus strain sp. IGTS8, this amount is not sufficient to maximize the desulfurization rate. Thus, the rate of desulfurization of DBT by IGTS8 or enzymes thereof can be enhanced in the presence of an additional amount of the flavin reductase.

The invention also includes a naturally-occurring homologue of the flavin reductase which is isolated from a source other than IGTS8 and which has substantially the same activity and physical properties as the flavin reductase. The term "homologue", as used herein, refers to a protein having at least about 50% sequence identity or homology with the reference protein or a protein of this type having one or more additional amino acids appended at the carboxyl terminus or amino terminus, such as a fusion protein. Such an enzyme can be produced by an organism, such as a microorganism, other than Rhodococcus strain sp. IGTS8. Suitable flavin reductase sources include other Rhodococcus strains, other desulfurizing microorganisms, such as Corynebacterium, and other bacteria. Such a flavin reductase can be isolated from such sources using standard techniques and assays, such as are described in the Exemplification and others known in the art. For example, the novel flavin reductase can be used to induce the formation of antibodies, such as monoclonal antibodies, according to known methods. The antibodies can then be used to purify the flavin reductase, or a homologue thereof, from an organism via, for example, affinity chromatography, as is well known in the art. Alternatively, the homologous flavin reductase can be cloned into a recombinant host cell by isolating an RNA or DNA molecule encoding the protein using standard hybridization techniques.

The invention further includes a non-naturally occurring homologue of the novel flavin reductase having a modified amino acid sequence resulting from the deletion, insertion or substitution of amino acid residues in the amino acid sequence of the native enzyme. Amino acid sequence variants of the native flavin reductase can be prepared by methods known in the art. For example, the desired polypeptide can be synthesized in vitro using known methods of peptide synthesis. The amino acid sequence variants are preferably made by introducing appropriate nucleotide changes into a DNA molecule encoding the native enzyme, followed by expression of the mutant enzyme in an appropriate vector, such as *E. coli*. These methods include site-directed mutagenesis or random mutagenesis, for example.

The two primary variables in the construction of amino acid sequence variants are (1) the location of the mutation site and (2) the nature of the mutation. These variables can be manipulated to identify amino acid residues at the active site of the enzyme. For example, an amino acid substitution which yields a mutant enzyme having significantly different activity than the native enzyme suggests that the substituted amino acid residue is at the active site. Such mutants can have increased or decreased activity relative to that of the native enzyme.

Amino acids can be modified, for example, by substituting first with a conservative choice, followed by non-conservative choices depending upon the results achieved, by deleting the target residue(s) or by inserting residues adjacent to a particular site. Variants can also be constructed using a combination of these approaches. Conservative substitutions are those in which a first amino acid residue is substituted by a second residue having similar side chain properties. An example of such a conservative substitution is replacement of one hydrophobic residue, such as valine, with another hydrophobic residue, such as leucine. A non-conservative substitution involves replacing a first residue with a second residue having different side chain properties. An example of this type of substitution is the replacement of a hydrophobic residue, such as valine, with an acidic residue, such as glutamic acid.

It is preferred to substitute amino acids which are not conserved among other flavin reductase. For example, the flavin reductase of the invention exhibits a degree of sequence homology with NADH:FMN oxidoreductases isolated from *Streptomyces pristinaespiralis* (Blanc et al., *J. Bact.*, 177 : 5206–5214 (1995)) and Chelatobacter strain ATCC 29600 (Uetz et al., *J Bact.*, 174 : 1179–1188 (1992)). In particular, amino acid residues which are common to all three enzymes are of possible importance in the catalytic process. These residues include Gly 57, Thr 59, Ala 60, Ser 62, Ser 65-Leu 68, Pro 70-Val 73, Thr 80, Ser 81, Leu 98, Gln 102, Ala 110, Phe 117, Thr 128, Gly 129, Pro 131, Gly 151-His 153, Gly 158 and Ala 172.

Amino acid deletions within the sequence generally range from 1 to about 30 residues, preferably from 1 to about 10 residues. Amino acid insertions include amino- and/or carboxyl-terminal fusions ranging in length from one residue to polypeptides containing 100 or more residues, resulting in the formation of a fusion protein. Intrasequence insertions (i.e., insertions within the flavin reductase amino acid sequence) can range generally from 1 to about 10 residues, preferably from 1 to about 5 residues and, more preferably, from 1 to about 3 residues.

The invention also includes a fragment of the novel flavin reductase enzyme or a homologue thereof. A fragment of this type generally comprises at least about 20 contiguous amino acids of the amino acid sequence of the flavin reductase or mutant. Such a fragment can be prepared by cleavage of an intact enzyme, for example, by treatment with a protease, or by expression of a DNA molecule encoding the fragment.

Generally, the mutant enzyme or variant possesses substantial sequence homology or identity with a native or "wild type" enzyme (i.e., essentially the same sequence). For example, substantial sequence homology includes enzymes which possess about 50% or greater, preferably about 70% or greater, and more preferably about 90% or greater, identical or conserved amino acids in an amino acid alignment.

In one embodiment, the flavin reductase is overexpressed by a desulfurization microorganism. This can be achieved, for example, by standard cloning techniques to overexpress the gene, as are described in Maniatis et al., *Molecular Cloning: A Laboratory Manual,* 2nd Edition (Cold Spring harbor Laboratory, Cold Spring Harbor, N.Y. (1989)), incorporated herein by reference (referred to hereinafter as "Maniatis et al."). Overexpression of the flavin reductase can also be accomplished by mutagenesis. Suitable mutagens include radiation, e.g., ultraviolet radiation, and chemical mutagens, such as N-methyl-N'-nitroso-guanidine, hydroxylamine, ethylmethanesulfonate and nitrous acid. The mutagenesis and subsequent screening for mutants harboring increased enzymatic activity can be conducted according to methods generally known in the art.

The present invention also includes an isolated nucleic acid sequence, such as a DNA or RNA sequence or molecule, which encodes a flavin reductase of the invention. Such a nucleic acid molecule can be naturally occurring, and isolated from an organism which produces the flavin reductase, such as Rhodococcus strain sp. IGTS8 or another bacterium. Such a nucleic acid molecule can also be isolated from an organism, such as a microorganism, other than Rhodococcus strain sp. IGTS8. Suitable sources of such a nucleic acid molecule include other Rhodococcus strains, other desulfurizing microorganisms, such as Corynebacterium, and other bacteria. The nucleic acid molecule can be isolated from such sources using standard techniques and assays, such as are described in the Exemplification and others known in the art. Such a nucleic acid molecule can also be synthesized in vitro using standard techniques. In one embodiment the nucleic acid molecule encodes the amino acid sequence depicted in SEQ. ID NO. 2 or a homologue thereof. For example, the nucleic acid molecule can include a DNA sequence such as is set forth in SEQ. ID NO. 1 or a DNA sequence which exhibits substantial identity with this sequence. Also included are DNA molecules which comprise a fragment of the DNA sequence set forth in SEQ. ID NO. 1, such as a fragment comprising at least about 20 contiguous nucleotides of SEQ. ID NO. 1.

The nucleic acid molecule can also be non-naturally occurring. A nucleic acid molecule of this type can be, for example, a mutant of a native nucleic acid molecule. The mutant can result from a silent mutation wherein the mutant nucleic acid encodes the same amino acid sequence as the corresponding native nucleic acid molecule. The mutant can also encode an amino acid sequence variant of the native flavin reductase, such as a substitution, deletion or insertion mutant as described above. Preparation of mutant nucleotide sequences can be accomplished by methods known in the art as are described in Old, et al., *Principles of Gene Manipulation,* Fourth Edition, Blackwell Scientific Publications (1989) and in Maniatis et al.

The invention further includes nucleic acid molecules which are useful as hybridization probes, which can be employed, for example, to isolate genes encoding the flavin reductase or a homologue thereof Such molecules comprise recombinant DNA molecules which hybridize to all or a fragment of the sequence of FIG. 1. Preferably, the molecules hybridize under stringent conditions, such as those set forth by Maniatis et al. For example, under conditions of high stringency, such as high temperatures and low salt concentration, only DNA molecules which are essentially exact matches will hybridize, particularly if the probe is relatively short. Hybridization under conditions of lower stringency, such as low temperatures, low concentrations of formamide and high salt concentrations, allows considerable mismatch between the probe and the target DNA molecule.

In yet another embodiment, the nucleic acid sequence of the present invention can be a DNA molecule resulting from the insertion into its chain, by chemical or biological means, of one or more genes encoding the flavin reductase described above and, optionally, a biocatalyst capable of selectively cleaving carbon—sulfur bonds, said genes not originally present in that chain. Recombinant DNA includes any DNA synthesized by procedures using restriction nucleases, nucleic acid hybridization, DNA cloning, DNA synthesis or any combination of the preceding. Methods of construction can be found in Maniatis et al., and additional methods are known by those skilled in the art.

The terms "plasmid" and "vector" are intended to encompass any replication competent plasmid or vector capable of having foreign or exogenous DNA inserted into it by chemical or biological means and subsequently, when transformed into an appropriate non-human host organism, of expressing the product of the foreign or exogenous DNA insert (i.e., of expressing the biocatalyst and flavoprotein of the present invention). In addition, the plasmid or vector must be receptive to the insertion of a DNA molecule or fragment thereof containing the gene or genes of the present invention, said gene or genes encoding a biocatalyst that selectively cleaves carbon—sulfur bonds in organosulfur compounds. Procedures for the construction of DNA plasmid vectors include those described in Maniatis et al. and others known by those skilled in the art.

The plasmids of the present invention include any DNA fragment containing a gene or genes encoding the flavin reductase and a biocatalyst that selectively cleaves carbon—sulfur bonds in organosulfur compounds. The DNA fragment should be transmittable, for example, to a host microorganism by transformation or conjugation. Procedures for the construction or extraction of DNA plasmids include those described in Maniatis et al., and others known by those skilled in the art.

The invention also includes a method of preparing a recombinant flavin reductase. For example, the enzyme can be made, and, preferably, overexpressed, in a recombinant microorganism which contains one or more copies of a DNA sequence which encodes the flavin reductase. In a particularly preferred embodiment, the recombinant organism also possesses one or more enzymes capable of catalyzing one or more reactions in the biodesulfurization of a fossil fuel, particularly DszA, DszB and/or DszC. For example, the DNA encoding the flavin reductase is simultaneously (e.g. presented in a single plasmid or vector) or independently transformed into a common host cell with the DNA encoding the desulfurization biocatalyst(s) or enzymes. The DNA encoding the flavin reductase can be, for example, under the control of the same or different promoter as the DNA encoding the biocatalyst capable of desulfurizing the fossil fuel. In one embodiment, the flavin reductase DNA is incorporated or ligated into the desulfurization gene cluster or operon of IGTS8, such that it is expressed with the desulfurization genes. The microorganism harboring the DNA sequence which encodes the flavin reductase can be grown under conditions which maximize the expression of the gene or genes.

Also included is a recombinant microorganism which contains a recombinant DNA molecule encoding the flavin reductase. In a particularly preferred embodiment, the recombinant microorganism encoding the flavin reductase also possesses enzymes capable of desulfurizing a fossil fuel. For example, the DNA encoding the flavin reductase can be transformed into a microorganism capable of desulfurizing a fossil fuel. In another example, the DNA encoding the flavin reductase is simultaneously or independently transformed into a common host cell with the DNA encoding a desulfurization biocatalyst. The DNA encoding the flavin reductase can be, for example, under the control of the same or different promoter as the DNA encoding the biocatalyst capable of desulfurizing the fossil fuel. As discussed above, the invention described herein relates in one aspect to a DNA molecule or fragment thereof containing a gene or genes which encode a flavin reductase and/or a biocatalyst capable of desulfurizing a fossil fuel that contains organosulfur compounds. The DNA molecule or fragment thereof can be purified and isolated DNA obtained from, e.g., a natural source, or can be recombinant (heterologous or foreign) DNA that is, for example, present in a non-human host organism. The DNA can be isolated by well-known techniques, such as PCR, designing oligonucleotide primers from the nucleotide sequence set forth in FIG. 1.

The transformed non-human host organisms of the present invention can be created by various methods by those skilled in the art. For example, electroporation, as explained by Maniatis et al., can be used. By the term "non-human host organism" is intended any non-human organism capable of the uptake and expression of foreign, exogenous or recombinant DNA. Preferably, the host organism is a bacterium, more preferably a pseudomonad. Another preferred host organism is Rhodococcus sp. IGTS8.

In the biocatalytic desulfurization stage, the liquid fossil fuel containing sulfur-bearing heterocycles is combined with the biocatalyst and the flavin reductase. The relative amounts of biocatalyst and flavin reductase and liquid fossil fuel can be adjusted to suit particular conditions, or to produce a particular level of residual sulfur in the treated, deeply desulfurized fossil fuel. The amount of biocatalyst preparation to be combined with a given quantity of liquid fossil fuel will reflect the nature, concentration and specific activity of the particular biocatalyst used, as well as the nature and relative abundance of inorganic and organic sulfur compounds present in the substrate fossil fuel and the degree of deep desulfurization sought or considered acceptable.

The method of desulfurizing a fossil fuel of the present invention involves two aspects. First, a host organism or biocatalytic preparation obtained therefrom is contacted with a fossil fuel to be desulfurized. This can be done in any appropriate container, optionally fitted with an agitation or mixing device. The mixture is combined thoroughly and allowed to incubate for a sufficient time to allow for cleavage of a significant number of carbon—sulfur bonds in organosulfur compounds, thereby producing a desulfurized fossil fuel. In one embodiment, an aqueous emulsion or microemulsion is produced with an aqueous culture of the organism or enzyme fraction and the fossil fuel, allowing the organism to propagate in the emulsion while the expressed biocatalyst cleaves carbon—sulfur bonds.

Variables such as temperature, mixing rate and rate of desulfurization will vary according to the organism biocatalyst used. Optimal parameters can generally be determined through no more than routine experimentation.

Several suitable techniques for monitoring the rate and extent of desulfurization are well-known and readily available to those skilled in the art. Baseline and time course samples can be collected from the incubation mixture, and prepared for a determination of the residual organic sulfur in the fossil fuel. The disappearance of sulfur from organosulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

The process and the biocatalytic compositions (including the recombinant microorganisms) of the claimed invention result in a significant and unexpected improvement over earlier disclosed biodesulfurization processes. It has been shown that in vitro the reactions catalyzed by purified DszA and DszC proteins are activated by the addition of the flavin reductase. This is particularly unexpected in view of recent discussions in the literature suggesting that FAD binds directly to DszC (Denome et al., *J. Bact.,* 176 : 6707–6716 (1994)) and the suggestion that NADH is the only cofactor required for the system (Oshiro et al., *FEMS Microbiol. Lett.,* 118 : 341–344 (1994)). Others suggest that DszABC are the sole enzymes responsible for desulfurization (Piddington et al. (1995), supra).

Without being limited to any particular mechanism or theory, it is believed that the pathway of the desulfurization reaction is set forth below:

Here the flavin reductase provides an electron transport chain which delivers, via $FMNH_2$, the reducing equivalents from NADH (or other electron donor) to the enzymes DszC (or Sox C) and/or DszA (or Sox A). The enzyme DszC is responsible for the biocatalysis of the oxidation reaction of DBT to $DBTO_2$. The enzyme DszA is believed to be responsible for the reaction of $DBTO_2$ to 2-(2-hydroxyphenyl) benzenesulfinate (HPBS).

As such, it is particularly preferred to add the cofactor, FMN, to the reaction medium as well as an electron donor, NADH.

The invention will now be further illustrated by the way of the following examples.

EXEMPLIFICATION

Isolation of Flavin Reductase from Rhodococcus Rhodococcus strain sp. IGTS8 cells containing the pENOK3 plasmid (Piddington et al., supra) were washed and suspended in 25 mM $Na_3PO_4$, pH 7.4, containing 100 mM NaCl, 0.5 mM dithiothreitol (DTT), 1 mM PMSF and 1 mg/mL DNAse. The suspension was passed through an ice cold Aminco French pressure cell at 20,000 psi to rupture the cells. Cell debris and unbroken cells were removed by centrifugation at 10,000×g for 45 minutes. All subsequent chromatographic steps were performed using a Pharmacia FPLC system at 4° C. The supernatant from above was applied to a Q-sepharose FastFlow (Pharmacia Biotech, Uppsala, Sweden) column which was washed extensively with 25 mM $Na_3PO_4$, pH 7.4, 100 mM NaCl, 0.5 mM DTT.

The column was developed with a linear gradient from 100 mM NaCl to 450 mM NaCl. FMN-dependent NADH oxidation activity was measured for each fraction. Flavin reductase activity was measured by the FMN-dependent oxidation of NADH monitored at 340 nm. The reaction was in 25 mM $Na_3PO_4$, pH 7.2, containing 100 mM NaCl, 0.5 mM DTT and 200 $\mu$M NADH. The background rate of NADH oxidation was measured for 30 seconds followed by the addition of FMN to a final concentration of 10 $\mu$M. Rates were expressed as nmol NADH oxidized per minute using the extinction coefficient of 6.22 $mM^{-1}cm^{-1}$. Those fractions containing activity were pooled, dialyzed overnight vs. 25 mM Na3PO4, pH 7.4, 100 mM NaCl, 0.5 mM DTT and applied to a Dyematrex Gel Green A column (Amicon, Inc., Beverly, Mass, U.S.A.) connected in-line with a Source 30Q (Pharmacia) anion exchange column. After washing the columns with two column volumes of buffer, the dye ligand column was disconnected and the Source 30Q column was developed with a linear salt gradient from 100 mM to 400 mM NaCl. Active fractions were pooled and made 1.7 M in $(NH_4)_2SO_4$ and applied to a Toyopearl Phenyl 650-M hydrophobic interaction column (TosoHaas). The column was developed with a linear gradient from 1.7 M-0 M $(NH_4)_2SO_4$. Active fractions were pooled, concentrated and further fractionated on Superdex75 in 25 mM $Na_3PO_4$, pH 7.2, containing 100 mM NaCl and 0.5 mM DTT. SDS-PAGE analysis of the final preparation showed a single band with an approximate molecular weight of 25,000 Da. The final preparation had a specific activity of 12,000 nmol NADH oxidized $min^{-1}$ (mg protein)$^{-1}$, a 2400-fold purification over the lysate.

The degree of purification resulting from each step of the procedure is presented in the table.

TABLE

| Step | [protein] (mg/mL) | Vol (mL) | Total Protein (mg) | SA* nmol-$min^{-1}$-$mg^{-1}$ | Total Activity | Fold Purification |
|---|---|---|---|---|---|---|
| French Press | 15.5 | 194 | 3000 | 5 | 15000 | |
| Q-sepharose | 2.15 | 105 | 226 | 48 | 10848 | 9.6 |

TABLE-continued

| Step | [protein] (mg/mL) | Vol (mL) | Total Protein (mg) | SA* nmol-min$^{-1}$-mg$^{-1}$ | Total Activity | Fold Purification |
|---|---|---|---|---|---|---|
| Source 30Q | 0.39 | 7 | 2.7 | 851 | 5957 | 170 |
| Superdex75 | 0.08 | 0.1 | 0.008 | 12000 | 960 | 2400 |

*Activity is NADH:FMN oxidoreductase

Complementation of DszA and DszC by Flavin Reductase

The ability of the flavin reductase to complement DszA and DszC activity was determined by measuring the rate of substrate turnover of each enzyme as a function of the flavin reductase concentration. Purified DszA and DszC were added to a solution of 200 mM DBTO$_2$ or 200 mM DBT, respectively, 10 mM FMN and 4 mM NADH in 25 mM Na$_3$PO$_4$ buffer, pH 7.2, 100 mM NaCl, 0.5 mM DTT and 0.02% Triton X-100. At the designated time points aliquots were removed and the reaction quenched with acetonitrile. Substrate and product concentrations were determined by HPLC using a Hypersil Phenyl analytical column.

Figure 2:
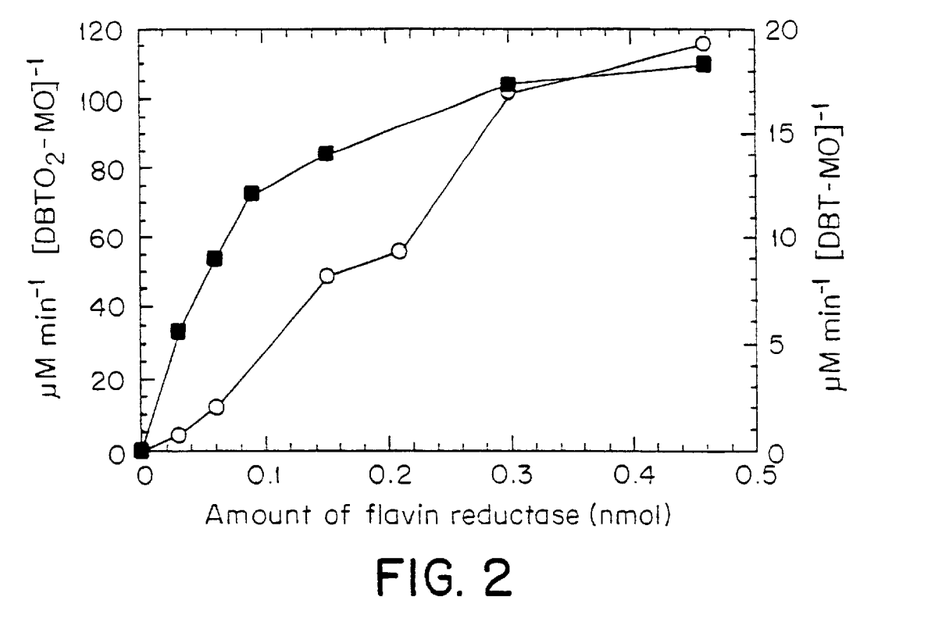
FIG. 2 illustrates the activation of DszA and DszC by purified Rhodococcus NADH:FMN oxidoreductase (flavin reductase). Fixed amounts of DszC (0.42 nmol) and DszA (0.2 nmol) were titrated with increasing amounts of the oxidoreductase and assayed for the conversion of DBT to DBTO$_2$ and DBTO$_2$ to 2-(2-hydroxyphenyl)benzenesulfinate (HPBS), respectively. Initial rates were calculated for each reaction and converted to specific activities (mM min$^{-1}$(nmol enzyme)$^{-1}$) and plotted versus the amount of flavin reductase added.

The results of the complementation experiments are shown in FIG. 2, which is a graph of the rate of substrate turnover by each of DszA and DszC as a function of the flavin reductase concentration. Both cases show saturation kinetics, and, on a molar basis, approximately the same amount of reductase was required for full activity of both enzymes.

Amino Acid Sequence Analysis of Flavin Reductase

Protein microsequencing from nitrocellulose blocks was performed using a standard procedure. Analysis of the N-terminal region resulted in the following amino acid sequence: SDKPNAVSSH TTPDVPEVAA TPELSTGI(A)A GDYRAALR(S)(H) (SEQ ID NO: 3). The protein was partially digested with trypsin and the resulting fragments were separated by HPLC. Several fragments were then sequenced, yielding the following sequences:
1. VHAEEDDESAAAPLLY(Y)(E)(G) (SEQ ID NO: 4)
2. YYXPTPL (SEQ ID NO: 5)
3. YYRPTPLGQK (SEQ ID NO: 6)

Cloning of the frr gene from Rhodococcus strain sp. IGTS8

Synthetic degenerate DNA oligonucleotides to be used as PCR primers and a probe were made base on the N-terminal and internal protein sequence determined as described above. These were
(1) PCR forward primer: 5'GAYAARCCNAAYGCNGT 3' (SEQ ID NO: 7)
(2) Probe: 5'CAYACNACNCCNGAYGT 3' (SEQ ID NO: 8)
(3) PCR reverse primer: 5'TCRTCRTCYTCYTC-NGCRTG 3' (SEQ ID NO: 9)

These oligonucleotides anneal to the frr DNA.

The PCR primers were used with genomic DNA from Rhodococcus strain sp. IGTS8 as the template. The PCR products were separated on a polyacrylamide gel and probed with $^{32}$P-labelled oligonucleotide 2 to determine which band contained the frr sequence. The probe does not overlap either of the PCR primers so that it should only hybridize in the band containing the frr sequence. The band that hybridized to the radioactive probe was cloned into the TA cloning vector pCRTM2.1, from Invitrogen. The DNA inserts were reprobed and a clone with the partial sequence of frr was selected.

In order to obtain the complete frr gene from the genomic DNA, the partial frr DNA sequence was labelled with $^{32}$p and used to probe a BamH I digest of genomic DNA. A band of about 5 kb was found to hybridize to this probe. This band was isolated from the gel and cloned into the BamH I site of pUC18. The frr gene contained in this fragment was sequenced. The gene has the unusual initiation codon TTG and codes for a protein of 191 amino acids with a molecular weight of 20,384 Da. The gene was sequenced and shown to have the nucleotide (SEQ ID NO: 1) and deduced amino acid (SEQ ID NO: 2) sequence depicted in FIG. 1.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of desulfurizing a fossil fuel containing organosulfur molecules, comprising the steps of:
   (a) contacting the fossil fuel with an aqueous phase containing a biocatalyst which oxidatively cleaves carbon—sulfur bonds and a rate-enhancing amount of a protein having NADH:FMN oxidoreductase activity and having the amino acid sequence set forth in SEQ ID NO. 2 or enzymatically active mutant thereof, thereby forming a fossil fuel and aqueous phase mixture;
   (b) maintaining the mixture under conditions sufficient for cleavage of the carbon—sulfur bonds or the organic sulfur molecules by the biocatalyst, thereby resulting in a fossil fuel having a reduced organic sulfur content; and (c) separating the fossil fuel having a reduced organic sulfur content from the resulting aqueous phase.

2. The method of claim 1 further comprising the steps of adding flavin and NADH.

3. The method of claim 1 wherein the fossil fuel is a liquid hydrocarbon.

4. The method of claim 1 wherein the biocatalyst capable of cleaving carbon—sulfur bonds is a cell-free fraction.

5. The method of claim 4 wherein the biocatalyst is a cell-free fraction of Rhodococcus strain sp. IGTS8.

6. The method of claim 1 wherein the biocatalyst comprises one or more enzymes or enzyme fractions derived from a microorganism having the capability of cleaving carbon—sulfur bonds.

7. The method of claim 6 wherein the microorganism is Rhodococcus strain sp. IGTS8.

8. The method of claim 1 wherein the biocatalyst capable of cleaving carbon—sulfur bonds and the flavin reductase are recombinantly produced by a single microorganism.

9. The method of claim 8 wherein the recombinant DNA is derived from Rhodococcus strain sp. IGTS8.

10. A method of enhancing the rate of oxidizing an organosulfur compound of a carbonaceous material containing organosulfur compounds, comprising the steps of:

(a) contacting the carbonaceous material with an aqueous phase containing a biocatalyst capable of oxidizing organosulfur compound and a rate-enhancing amount of a flavin reductase having the amino acid sequence set forth in SEQ. ID NO. 2 or an enzymatically active mutant thereof;

(b) maintaining the mixture of step (a) under conditions sufficient for the reaction of the organosulfur compounds catalyzed by the biocatalyst.

11. The method of claim 10 wherein the NADH:FMN oxidoreductase is of Rhodococcus origin.

12. The method of claim 11 wherein the flavin reductase is isolated from Rhodococcus strain IGTS8.

* * * * *